(12) United States Patent
Hartmann et al.

(10) Patent No.: US 6,406,532 B1
(45) Date of Patent: Jun. 18, 2002

(54) TITANIUM DIOXIDE POWDER WHICH CONTAINS IRON OXIDE

(75) Inventors: Werner Hartmann, Babenhausen; Dieter Kerner, Hanau, both of (DE)

(73) Assignee: Degussa Aktiengesellschaft, Frankfurt am Main (DE)

( * ) Notice: Subject to any disclaimer, the term of this patent is extended or adjusted under 35 U.S.C. 154(b) by 1333 days.

(21) Appl. No.: 08/528,044

(22) Filed: Sep. 14, 1995

Related U.S. Application Data

(63) Continuation of application No. 08/181,426, filed on Jan. 14, 1994, now abandoned.

(30) Foreign Application Priority Data

Feb. 2, 1993 (DE) .......................................... 43 02 896

(51) Int. Cl.[7] .......................... C01G 23/04; A61K 7/42
(52) U.S. Cl. ...................... 106/439; 106/456; 424/59; 424/647; 424/648
(58) Field of Search ................... 106/439, 456; 424/59, 647, 648

(56) References Cited

U.S. PATENT DOCUMENTS

| | | | |
|---|---|---|---|
| 3,926,659 A | 12/1975 | Bernhard | 106/418 |
| 4,297,143 A | 10/1981 | Kleinschmit | 501/103 |
| 4,916,107 A | 4/1990 | Brand | 502/309 |
| 5,837,050 A | * 11/1998 | Okuda et al. | 106/439 |

FOREIGN PATENT DOCUMENTS

| | | |
|---|---|---|
| DE | 2313331 | 9/1974 |
| EP | 0023587 | 11/1981 |
| EP | 0241647 | 10/1987 |
| EP | 0317875 | 5/1989 |
| JP | 5-330825 | * 12/1993 |

OTHER PUBLICATIONS

Derwent Abstract AN 94–022607 for JP-A-5 330 825, Dec. 1993.
Patent Abstracts of Japan, vol. 15, No. 440 (C–0883) Nov. 11, 1991 for JP-A-03 186 348.
Patent Abstracts of Japan, vol. 13, No. 260 (C–607) Jun. 15, 1989 for JP-A-01 061 325.
Hattori, et al., Bul. Chem. Soc. Jpn., 56, 3208–3215 (1983).

* cited by examiner

Primary Examiner—C. Melissa Koslow
(74) Attorney, Agent, or Firm—Pillsbury Winthrop LLP

(57) ABSTRACT

A titanium dioxide powder/iron oxide mixed oxide which is prepared from $FeCl_3$ and $TiCl_4$ using a pyrogenic, especially a flame hydrolytic method. A further possibility is to coat pyrogenically, especially flame hydrolytically prepared titanium dioxide with iron oxide in aqueous dispersion. Both of these titanium dioxide powders which contain iron oxide may be used as a UV absorber in sunscreens.

3 Claims, 2 Drawing Sheets

TITANIUM DIOXIDE POWDER WHICH CONTAINS IRON OXIDE

Figure 1:
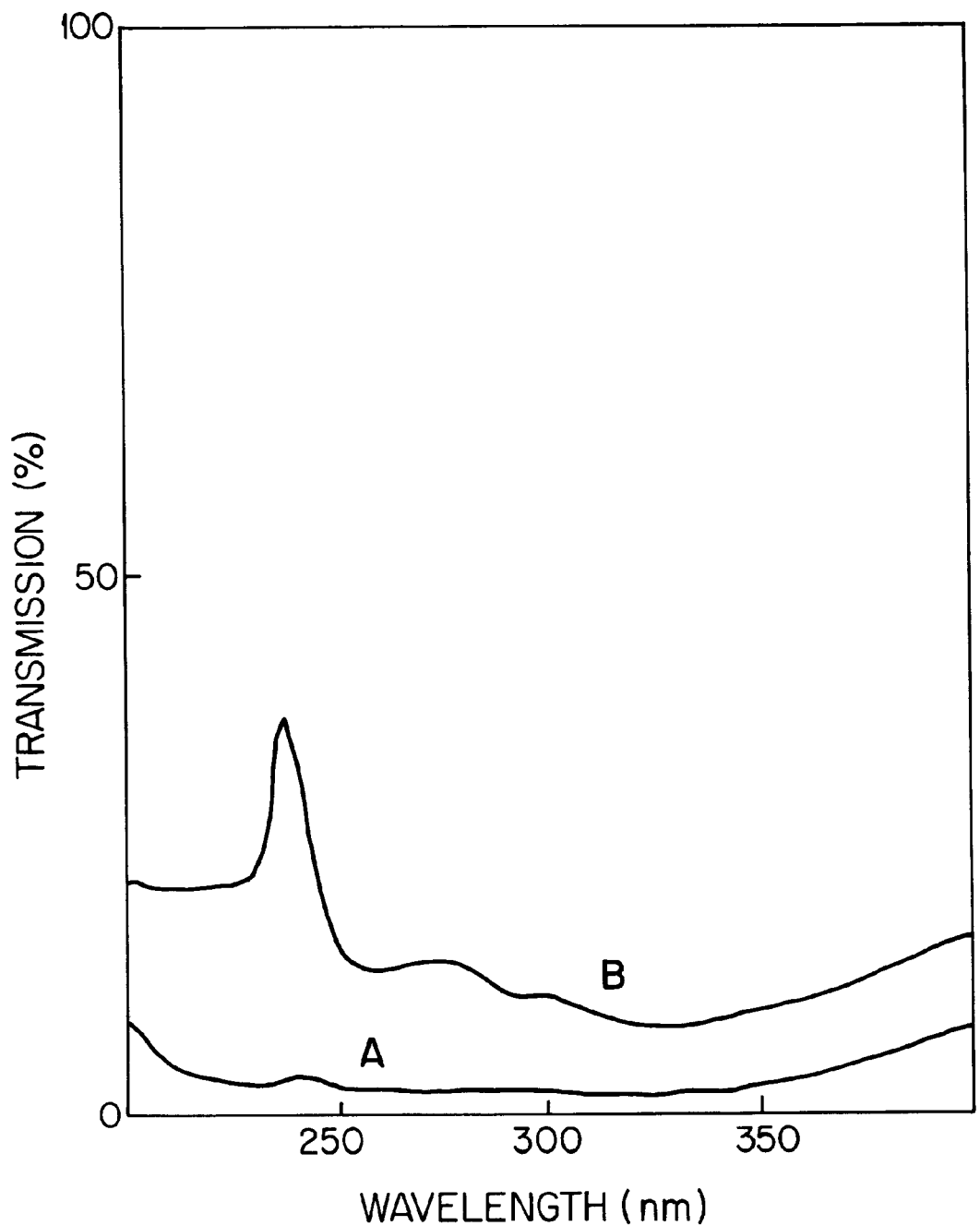

This is a continuation of Application No. 08/181,426, filed on Jan. 14, 1994 which was abandoned.

The present invention relates to titanium dioxide powder which contains iron oxide, a process for its preparation and use.

BACKGROUND OF THE INVENTION

It is known that titanium dioxide can be prepared using a pyrogenic method, particularly using a flame hydrolysis method (see Published German Patent Application DE-PS 830 786). Titanium dioxide prepared in this way may be used in sunscreens as a UV absorbing agent which is simultaneously transparent to visible light. A further area of use comprises lacquers and plastics. The preparation of mixed oxides using a pyrogenic method is known from Published German Patent Applications DE-A 952 891, DE-A 29 31 585, DE-A 29 31 810 (U.S. Pat. No. 4,297,143) and DE-A 36 11 449.

For special applications, such as e.g. as a UV absorbing agent in sunscreens, there is a need for a material which has a particularly high capacity for absorbing for UV irradiation and a transparency which cannot be achieved with known titanium dioxide.

SUMMARY OF THE INVENTION

The present invention provides titanium dioxide powder which contains iron oxide. The present invention also provides a titanium dioxide powder which contains iron oxide and which comprises an iron oxide/titanium dioxide mixed oxide with a BET surface area of 10 to 150 m$^2$/g, which contains 0.5 to 50 wt. % of iron oxide, with reference to the total amount of mixed oxide, as a component of the mixed oxide, prepared by a pyrogenic, in particular by a flame hydrolytic method.

The iron oxide/titanium dioxide mixed oxide can be prepared by evaporating anhydrous iron(III) chloride, transferring the evaporated anhydrous iron(III) chloride, together with an inert gas, e.g. nitrogen, into the mixing chamber of a burner of known design, mixing it there with hydrogen, air and gaseous titanium tetrachloride in a ratio which corresponds to the composition of the iron/titanium mixed oxide, burning the 4-component mixture in a reaction chamber, then separating the solid titanium dioxide mixed oxide from the gaseous reaction products and optionally removing adhering hydrogen chloride in moist air.

In a preferred embodiment, the titanium dioxide powder which contains iron oxide (iron oxide/titanium dioxide mixed oxide) may have the following physical-chemical properties:

| Iron oxide content | (wt. %) | 0.5–50 |
|---|---|---|
| Specific surface area | (m$^2$/g) | 10–150 |
| Primary particle size | (nm) | 5–100 |
| Tamped density | (g/l) | 100–300 |
| Loss on ignition (2 h 1000° C.) | (wt. %) | 0.5–5 |
| Chloride content | (wt. %) | <1 |

The iron oxide/titanium oxide mixed oxide of the invention is very finely divided, very homogeneous and very pure. It possesses better absorption for UV light with extensive transparency for visible light, as compared with the prior art. It is readily dispersible in the appropriate medium, for example a sunscreen.

The iron oxide/titanium dioxide mixed oxide powder of the invention may be used to prepare cosmetic articles, lacquers, catalysts and photocatalysts, as a UV absorber.

The invention also provides a titanium dioxide powder which contains iron oxide which is a pyrogenically, in particular flame hydrolytically, prepared titanium dioxide with a primary particle size of between 10 and 150 nm and which is coated with iron oxide, wherein the iron oxide fraction may be 0.1 to 20 wt. %, with reference to the whole powder.

In a preferred embodiment of the invention, the iron oxide coated titanium dioxide powder may have the following physical-chemical properties:

| Iron oxide content | (wt. %) | 0.1–20 |
|---|---|---|
| Specific surface area | (m2/g) | 10–100 |
| Tamped density | (g/l) | 300–800 |
| Loss on ignition (2 h 1000° C.) | (wt. %) | 0.5–5 |

The iron oxide coated titanium dioxide powder of the invention can be prepared by dispersing pyrogenically, in particular flame hydrolytically, prepared titanium dioxide in an aqueous solution of an iron salt, optionally first neutralizing the dispersion, filtering, drying, washing, redispersing the washed filter cake and spray-drying and finally calcining the product obtained.

The solids content of the dispersion may be 10 to 30 wt. %. Iron(III) chloride, iron(III) nitrate, inter alia, for example, may be used as an iron salt.

Calcination may be performed at a temperature of 300 to 800° C.

This iron oxide coated titanium dioxide powder may be used to prepare cosmetic articles, lacquers, catalysts and photocatalysts and as a UV absorber.

The present invention also provides skin cosmetics which contain the above-described titanium dioxide powders which contain iron oxide, preferably in amounts of 0.05 to 10 wt. %. The titanium dioxide which contains iron oxide may be a pyrogenically, especially flame hydrolytically prepared iron oxide/titanium dioxide mixed oxide. Alternatively, or in addition thereto, the titanium dioxide which contains iron oxide may be a pyrogenically prepared titanium dioxide coated with iron oxide.

DETAILED DESCRIPTION OF PREFERRED EMBODIMENTS

The following examples illustrate the practice of the present invention.

EXAMPLE 1

FeCl$_3$ and TiCl$_4$ are volatilized in two separate evaporators (evaporating temperatures: FeCl$_3$ 400° C., TiCl$_4$ 200° C.). The chloride vapors are introduced into the mixing chamber of a burner by means of nitrogen. There they are mixed with hydrogen and dry air and/or oxygen and burned in a reaction chamber. The reaction products are cooled to about 100° C. in the coagulation section. The mixed oxides obtained are then separated out using a filter. Adhering chloride is removed by treating the mixed oxides with moist air at temperatures between 500 and 700° C. The reaction conditions and properties of the product for various mixed oxides are given in Table 1.

TABLE 1

Iron/titanium mixed oxides

| No. | TiCl$_4$ (g/h) | FeCl$_3$ (g/h) | H$_2$ (l/h) | Air (l/h) | Fe$_2$O$_3$ (%) | BET (m$^2$/g) | Tamped Density (g/l) | Loss on Ignition (%) | Chloride Content |
|---|---|---|---|---|---|---|---|---|---|
| 1 | 1717 | 14  | 525 | 3079 | 0.9  | 51 | 185 | 2.1 | 0.25 |
| 2 | 1687 | 47  | 525 | 3079 | 3.1  | 47 | 190 | 2.1 | 0.44 |
| 3 | 1613 | 107 | 525 | 3079 | 7.2  | 46 | 185 | 1.7 | 0.36 |
| 4 | 1577 | 161 | 525 | 3079 | 10.7 | 47 | 180 | 1.9 | 0.35 |
| 5 | 1424 | 326 | 525 | 3079 | 21.1 | 49 | 180 | 1.8 | 0.25 |

Measuring the UV Absorption

To measure the UV absorption or transmission, mixed oxide no. 2 (3% Fe$_2$O$_3$) is dispersed in a mixture which contains 3 parts of isopropyl myristate and 7 parts of vaseline. The mixed oxide fraction is 0.25 wt. %. Then the dispersion is arranged in a 0.2 mm thick layer between two quartz plates. The transmission is measured with a Shimazu UV-201A spectrometer. Pyrogenic titanium dioxide P 25 (BET surface area 50 m$^2$/g) is used as a comparison substance and tested under the same conditions.

FIG. 1 shows the variation of transmission as a function of wavelength as % in the region from 200 to 400 nm (curve A: mixed oxide no. 2, curve B: titanium dioxide P 25). The dispersion with the mixed oxide demonstrates a much lower transmission than the dispersion which contains pure titanium dioxide P 25.

Thus the mixed oxide offers outstanding protection against UV rays.

Titanium dioxide P 25 (Manufacturer: Degussa AG) is a titanium dioxide prepared from TiCl$_4$ using a pyrogenic method. It has the following physical-chemical properties:
Physical-chemical properties:

| | | |
|---|---|---|
| Titanium dioxide P 25 BET surface area | m$^2$/g | 50 ± 15 |
| Average size of primary particles | nm | 30 |
| Tamped density (DIN 53 194) | g/l | ca. 150 |
| Loss on drying* (DIN 53 198, method A) (2 hours at 105° C.) | % | <1.5 |
| Loss on ignition **(DIN 52 911) (2 hours at 1000° C.) | % | <2 |
| pH (in 4% strength aqueous dispersion) (DIN 53 200) | | 3–4 |
| X-ray structure | | predominantly anatase |
| Isoelectric point at pH | | 6.6 |
| Density | g/cm3 | 3.8 |
| Al$_2$O$_3$** | % | <0.3 |
| TiO$_2$** | % | >97 |
| SiO$_2$ | % | <0.2 |
| Fe$_2$O$_3$ | % | <0.01 |
| HCl | % | <0.3 |

*on leaving the factory
**with respect to the substance dried for 2 hours at 105° C.

EXAMPLE 2

34 g of FeCl$_3$. 6H$_2$O are dissolved in 800 ml of water. 200 g of pyrogenic titanium dioxide P 25 (BET surface area 50 m2/g) are introduced into the solution with intensive stirring. The resulting suspension is then spray-dried. Afterwards, the powder is calcined for two hours at a temperature of 600° C. The mixed oxide contains 5 wt. % of iron oxide and has a specific surface area of 41 m$^2$/g.

BRIEF DESCRIPTION OF FIGURES OF DRAWING

Figure 2:
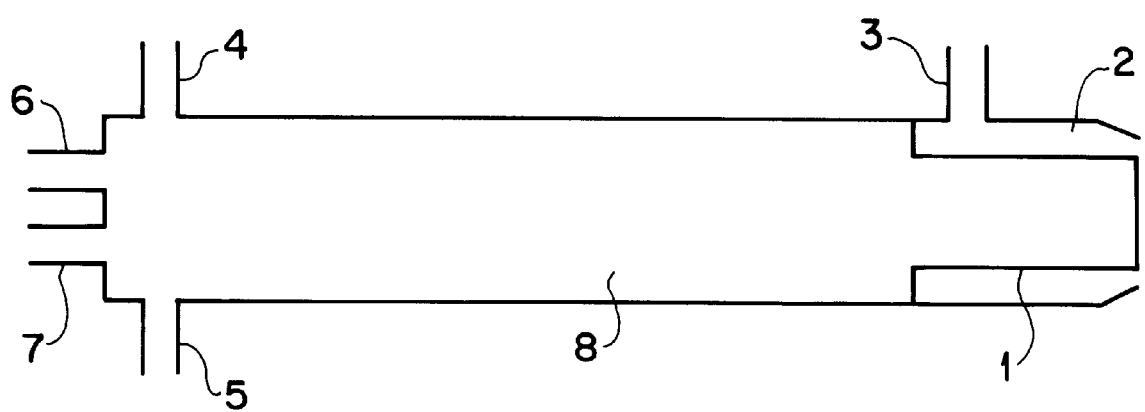

FIG. 1 is a graph which shows the variation of transmission as a function of wavelength for the mixed oxide of Example 1; and FIG. 2 is a schematic view of a burner which can be used to carry out the process of the present invention.

In carrying out the invention in the apparatus shown in FIG. 2, the gas-forming metal chlorides, i.e., titanium tetrachloride and iron(III) chloride are volatilized and introduced with an inert gas through the inlets 4 and 5 into the mixing chamber 8. Hydrogen and dried air are preheated and introduced through the inlets 6 and 7 into the mixing chamber 8. The four component mixture is advanced into the inside of the burner 1 of the burner and burned in a flame. In order to sustain the flame, an additional quantity of hydrogen can be supplied through the annular chamber 2 which surrounds the inside of the burner 1.

What is claimed is:

1. A process for preparing a titanium dioxide powder composition, the process comprising volatalizing anhydrous iron (III) chloride together with an inert gas, transferring the volatalized anhydrous iron (III) chloride to the mixing chamber of a burner, mixing the volatalized iron (III) chloride in the burner with hydrogen, air and gaseous titanium tetrachloride in a ratio which corresponds to the composition of the iron oxide/titanium dioxide mixed oxide, burning the 4-component mixture in a reaction chamber of said burner and separating the solid iron oxide/titanium dioxide mixed oxide from the gaseous reaction product, thereby producing a flame hydrolytically prepared iron oxide/titanium dioxide mixed oxide with a BET surface area of 10 to 150 m$^2$/g, which contains 0.5 to 50 wt. % of iron oxide, with reference to the total amount, as a component of the mixed oxide.

2. A process as set forth in claim 1 including the step of removing adhering hydrogen chloride in moist air.

3. A skin cosmetic containing a flame-hydrolytically prepared titanium dioxide component which contains iron oxide in an amount of about 0.05 to about 10 wt. % of the titanium dioxide component.

* * * * *